United States Patent

Lunts et al.

[11] 4,000,192
[45] Dec. 28, 1976

[54] PHARMACOLOGICALLY ACTIVE COMPOUNDS

[75] Inventors: Lawrence Henry Charles Lunts; David Hartley, both of London, England

[73] Assignee: Allen & Hanburys Limited, London, England

[22] Filed: May 6, 1974

[21] Appl. No.: 467,211

[30] Foreign Application Priority Data

May 7, 1973 United Kingdom ............ 22004/73

[52] U.S. Cl. .................... 260/559 S; 260/559 A
[51] Int. Cl.[2] ................................ C07C 103/22
[58] Field of Search ................. 260/559 S, 559 A

[56] References Cited

UNITED STATES PATENTS

| 3,483,221 | 12/1969 | Wilhelm et al. .......... 260/326.14 T |
| 3,644,353 | 2/1972 | Lunts et al. ................ 260/559 S |
| 3,644,520 | 2/1972 | Hartley et al. ................ 260/559 |

FOREIGN PATENTS OR APPLICATIONS

| 6,919,614 | 7/1970 | Netherlands .................. 260/559 S |
| 1,260,521 | 1/1972 | United Kingdom |
| 1,266,058 | 3/1972 | United Kingdom |

OTHER PUBLICATIONS

Crowther et al., J. Med. Chem., vol. 11, pp. 1009–1013 (1968).
Howe et al., J. Med. Chem., vol. 11, pp. 1000–1008 (1968).
Grana et al., Il Farmaco Ed. Soc., vol. XXI, pp. 4–15, (1966).

Primary Examiner—C. Davis
Attorney, Agent, or Firm—Bacon & Thomas

[57] ABSTRACT

Compounds of the formula

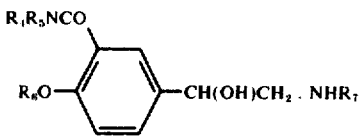

in which:
 $R_4$ and $R_5$ independently represent hydrogen or lower alkyl;
 $R_6$ represents a group $Y(CH_2)_n$, in which n is 2 or 3 and
 Y represents a straight or branched chain alkyl group containing 5 carbon atoms optionally substituted with one more hydroxy or alkoxy groups or by aryl groups which may, in turn, contain hydroxy or alkoxy substituents; or
 Y represents a group ZO—, in which Z represents a straight or branched alkyl group containing from 2 to 6 carbon atoms inclusive substituted by one or more alkoxy, hydroxy, or aryloxy groups; or Z represents an aryl group which may, optionally, contain one or more hydroxy or alkoxy substituents; and
 $R_7$ represents a straight or branched alkyl group containing from 3 to 6 carbon atoms, inclusive, optionally substituted by an aryl or aryloxy group which aryl or aryloxy group may, in turn be substituted by hydroxy and alkoxy groups and pharmaceutically acceptable salts thereof. These compounds have utility in the treatment of cardiovascular diseases.

11 Claims, No Drawings

PHARMACOLOGICALLY ACTIVE COMPOUNDS

This invention which is an improvement of that described in our U.K. specification No. 1,260,521 relates to phenylethanolamine derivatives having useful biological activity and to compositions containing the same.

In our prior U.K. specification No. 1,260,521 there are disclosed and claimed compounds of the general formula:

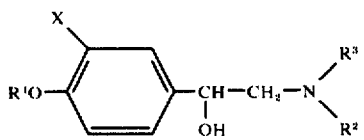

and physiologically acceptable acid addition salts, in which:

$R^1$ is a lower alkyl, lower alkenyl or arylalkyl radical, which radicals may optionally be substituted by one or more alkoxy or hydroxy groups;

$R^2$ represents a hydrogen atom or a lower alkyl radical which may optionally be substituted by one or more hydroxy groups, amino groups, or heterocyclic rings containing one or more heteroatoms or represents a cycloalkyl, arylalkyl or aryloxyalkyl radical, which radicals may optionally be substituted by one or more alkoxy or hydroxy groups;

$R^3$ represents a hydrogen atom or a benzyl group;

X represents a group of the formula $-CONR^4R^5$ where $R^4$ and $R^5$ which may be the same or different represent hydrogen or lower alkyl; with the proviso that when $R^2$ is tertiary butyl and $R^1$ is a benzyl group then $R^3$ represents a hydrogen atom.

It has now been found that certain compounds related to those of the above general formula show an unexpected selectivity in their pharmacological actions which makes their use in cariovascular diseases, e.g. angina pectoris, hypertension or cardiac arrhythmias, especially advantageous.

The compounds of the main patent are non-selective blockers of β-adrenoreceptors at both $β_1$ and $β_2$ sites. The blockade of $β_2$-adrenoreceptors in the lungs may give rise to bronchospasm, and the use of substances with this property is contra-indicated in patients with asthma or bronchitis where lung function is impaired.

The compounds of the present invention surprisingly show high potency in blocking adrenergic responses selectively at $β_1$ receptors, e.g. those in the heart, with minimal effects on $β_2$ receptors of the lung. They may therefore be used advantageously in patients with pulmonary disorders to avoid unwanted side-effects.

The invention therefore provides compounds of the general formula:

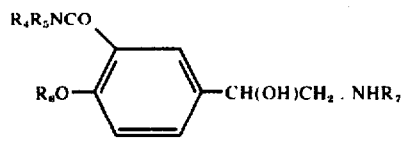

in which:

$R_4$ and $R_5$ independently represent hydrogen or lower alkyl; $R_6$ represents a group $Y(CH_2)_n$, in which n is 2 or 3 and Y represents a straight or branched chain alkyl group containing 5 carbon atoms optionally substituted with one or more hydroxy or alkoxy groups or by aryl groups which may, in turn, contain hydroxy or alkoxy substituents; or Y represents a group ZO —, in which Z represents a straight or branched alkyl group containing from 2 to 6 carbon atoms inclusive substituted by one or more alkoxy, hydroxy, aryloxy groups; or Z represents an aryl group which may, optionally, contain one or more hydroxy or alkoxy substituents; and $R_7$ represents a straight or branched alkyl group containing from 3 to 6 carbon atoms, inclusive, optionally substituted by an aryl or aryloxy group which, aryl or aryloxy group may, in turn, be substituted by hydroxy and alkoxy groups, and pharmaceutically acceptable salts thereof.

Suitable salts of the compounds of formula I include salts with organic or inorganic acids containing pharmaceutically acceptable anions, e.g. hydrochloric, maleic acid, etc.

A particular class of compounds according to the invention are those in which $R_4$ and $R_5$ are both hydrogen. Preferably the group $R_6$ represents, within the definitions given above, one of the following groups; $C_7$ or $C_8$ straight chained alkyl, alkoxyalkoxyalkyl, aryloxyalkyl, hydroxyaryloxyalkyl, alkoxyyaryloxyalkyl, acyloxyaryloxyalkyl, the group $R_7$ preferably represents aralkyl such as a group

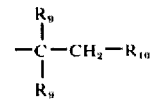

in which the group $R_9$ independently represent hydrogen or lower alkyl and $R_{10}$ represents benzyl.

A particularly preferred class of compounds according to the invention are those in which $R_4$ and $R_5$ are both hydrogen and preferably the group $R_6$ represents one of the following groups:- 2'-ethoxy-2-ethoxyethyl, 2-phenoxyethyl, 2-(4'-hydroxyphenoxy)ethyl, 2-(2' and 4'-ethoxyphenoxy)ethyl, heptyl, octyl, and $R_7$ preferably represents 1-methyl-3-phenylpropyl.

As the compounds of general formula I possess at least one asymmetric carbon atom, the invention also includes all the possible optically active forms and racemic mixtures of the compounds. Racemic compounds may be resolved by conventional methods, for example by salt formation with an optically active acid, followed by fractional crystallisation.

Mixtures of racemic compounds may be separated by fractional crystallisation of the bases or their acid addition salts.

The selective blockade of $β_1$ adrenoreceptors was demonstrated in the anaesthetized dog by the reduction of the tachycardia induced by isoprenaline, while at the same time having little effect on the lowering of blood pressure induced by isoprenaline.

The results given below in the table following the Example show that, unlike propranolol the standard nonselective β-blocker used in the treatment of angina and hypertension, the compounds of the invention, block the $β_1$ receptors in the heart, but not the $β_2$ receptors in peripheral circulation, which includes airways smooth muscle.

Thus the compounds of the invention have the advantage of being effective in the treatment of angina and hypertension while being less likely to induce bronchospasm.

The compounds may be formulated for use in human or veterinary medicine for therapeutic or prophylatic purposes. The invention therefore includes within its scope pharmaceutical compositions comprising as active ingredient compounds of general formula 1 or physiologically acceptable acid addition salts thereof. Preferred salts include the hydrochloride, sulphate, maleate, acetate, fumarate, lactate, and citrate. Such compositions may be presented for use in conventional manner with the aid of carriers or excipients and formulatory agents as required, and with or without supplementary medicinal agents. These compositions include, for instance, solid or liquid preparations for oral use, suppositories and injections. Oral administration is most convenient in the form of tablets which may be prepared according to conventional methods and may be coated if desired. Injections may be formulated with the aid of physiologically acceptable carriers and agents as solutions, suspensions, or as dry products for reconstitution before use. The doses of the active ingredient which may be used may vary generally within the range of 5 mg to 1000 mg, preferably 20 mg to 200 mg.

The compounds according to the present invention may be made by processes analogous to those described in the parent patent.

A particularly preferred process consists of in the catalytic hydrogenation of the ether of formula (II):

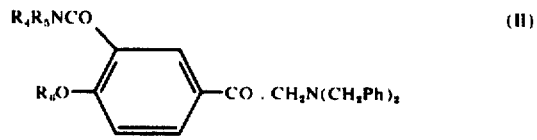

(in which $R_4$, $R_5$ and $R_6$ have the meanings given above) in the presence of a carbonyl compound e.g. an aldehyde or ketone yielding a group $R_7$. This catalytic hydrogenation is preferably effected in the presence of a supported noble metal catalyst such as palladium-charcoal or platinum-charcoal catalysts, or mixtures of these in a solvent with warming if necessary. This process involves hydrogenolysis of the benzyl groups, reductive alkylation of the so-formed primary amine, and reduction of the keto groups. One may also use as starting material the potential intermediates in this process that is to say the corresponding primary amine or the corresponding hydroxy dibenzylamino compound or the hydroxy primary amine. The ether (II) is preferably prepared by the alkylation of the parent ketone (III):

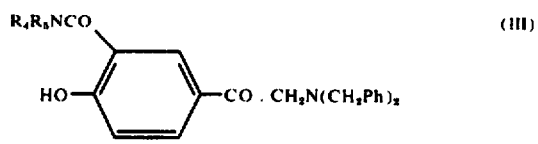

in which $R_4$ and $R_5$ have the above-stated meanings. Alkylation may be effected by standard procedures using an alkylating agent $R_6W$ in which $R_6$ has the meaning given above or is a group convertible thereto, for example a moiety with a protected hydroxy group and W may be for example a halogen atom or a tosyl group. The alkylation is preferably effected in a solvent in the presence of a base such as potassium carbonate or sodium hydride if necessary with heating. If desired, the sequence of the above reactions may be reversed and compounds of formula (I) may be prepared by the alkylation of corresponding phenols (I; $R_6$=H) by the methods before described.

Other methods which may be used are described in the main patent. Such methods include in particular the reduction of the ketone of the formula (IV):

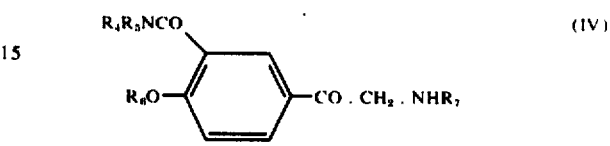

This compound may be made by condensation of the haloketone (V)

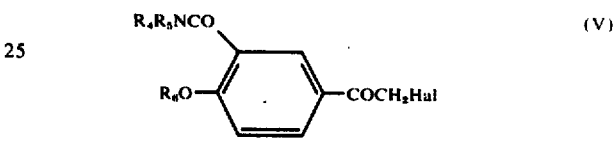

with an amine $R_7NH_2$. When an optically active amine is used, reduction of the resulting ketone yields a mixture of two diastereoisomers, which may separated as the base or as a salt, by for example, fractional crystallisation.

In the above processes the group $-CONR_4R_5$ may be present in the starting material or may be formed at any convenient stage from an alkoxycarbonyl group $-COOR_8$, where $R_8$ represent an alkyl group by reaction with an amine $HNR_4R_5$ (in the simplest case, ammonia).

The following Examples illustrate the invention:

EXAMPLE 1

2-[2-(2-Ethoxyethoxy)ethoxy]-5[1-hydroxy-2-[(1-methyl-3-phenylpropyl)amino]ethyl]benzamide hydrochloride a.

5-(N,N-Dibenzylglycyl)-2-[2-(2-ethoxyethoxy)ethoxy]benzamide

A solution of 5-(N,N-dibenzylglycyl)salicylamide (10 g.) in dimethylformamide (75 ml) was added dropwise to a stirred suspension of sodium hydride (0.875 g) in dimethylformamide (25 ml). 2-(2-Ethoxyethoxy)ethyl p-toluenesulphonate (12.75 g) was then added and the solution heated at 100° for 2 hours. The solvent was evaporated to give a yellow oily solid which was partitioned between ethyl acetate and water. The ethyl acetate layer was dried (MgSO₄), concentrated to 30 ml and chromatographed on alumina (60 g.). The column was eluted with ethyl acetate (100 ml portions). The first fraction was discarded and the subsequent four fractions yielded an oil (12.2 g) which crystallised from ethanol to give the ether as colourless plates (5.8 g) m.p. 91.5°–92.5°. Recrystallisation of a sample raised the m.p. to 92.5°–94°.

b.

2-[2-(2-Ethoxyethoxy)ethoxy]-5-[1-hydroxy-2-[(1-methyl-3-phenylpropyl)amino]ethyl]benzamide hydrochloride A solution of 5-(N,N-dibenzylglycyl)-2-[2-(2-ethoxyethoxy)ethoxy]benzamide (4.9 g) and benzyl acetone (1.7 g) in ethanol (100 ml) was hydrogenated in the presence of 5% platinum on charcoal (0.5 g) and 10% palladium on charcoal (0.5 g) catalysts for 48 hours. Catalysts and solvent were removed and the colourless oil that remained was treated with ethyl acetate and ethereal hydrogen chloride. The hydrochloride was collected (4.1 g), m.p. 126°–127°.

EXAMPLE 2

5-[1-Hydroxy-2-[(1-methyl-3-phenylpropyl)amino]ethyl]-2-(2-phenoxyethoxy)benzamide, hydrochloride a.

5-(N,N-Dibenzylglycyl)-2-(2-phenoxyethoxy)benzamide

A solution of the sodium salt from 5-(N,N-dibenzylglycyl)-salicylamide (10 g) and sodium hydride (0.7 g) in dimethylformamide (50 ml) was heated at 100° for 2 hours with 2-phenoxyethyl bromide (6 g.). The solution was evaporated under reduced pressure gave a yellow residue that was dissolved in ethyl acetate and water. The organic solution was washed three times with water, dried (MgSO$_4$) and evaporated to leave the crude ether as a yellow oily solid, which was recrystallised from ethanol (150 ml) to give colourless plates (4.6 g) m.p. 146°–147°.

b.

5-[1-Hydroxy-2-[1-methyl-3-phenylpropyl)amino]ethyl]-2-(2-phenoxyethoxy)benzamide, hydrochloride A solution of the above amide (3.0 g), benzyl acetone (1.0 g), and acetic acid (0.4 ml) in warm ethanol (150 ml) and methanol (100 ml) was hydrogenated in presence of 10% palladium on charcoal (0.5 g) and 5% platinum on charcoal (0.5 g). When the uptake of hydrogen (562 ml) had ceased, the catalysts and solvents were removed to leave a pale yellow oil which was treated in ethyl acetate (30 ml) with an excess ethereal hydrogen chloride to give a gum, which was triturated with dry ether to form the hydrochloride as a white solid (2.3 g) m.p. 162°–165°.

EXAMPLE 3

2-(Heptyloxy)-5-[1-hydroxy-2[(1-methyl-3-phenylpropyl)amino]ethyl]benzamide, hydrochloride a. 5-(N,N-Dibenzylglycyl)-2-(heptyloxy)benzamide

A mixture of potassium carbonate (3.73 g), 5-(N,N-dibenzylglycyl) salicylamide (10 g) and 1-iodo heptane (7.5 g) in butanone (200 ml) was stirred and heated under reflux for 24 hours. The solid was filtered off and the filtrate was evaporated. The residue was partitioned between ethyl acetate and water. The dried (MgSO$_4$) ethyl acetate solution was evaporated to give a yellow oil (12.6 g) which crystallised twice from isopropanol to yield the ether (6.3 g) m.p. 97.5°–98°.

b.

2-(Heptyloxy)-5-[1-hydroxy-2-[(1-methyl-3-phenylpropyl)amino]ethyl]benzamide hydrochloride A solution of 5-(N,N-dibenzylglycyl)-2-(heptyloxy)-benzamide (3 g) and benzyl acetone (1.034 g) in ethanol (100 ml) was hydrogenated in the presence of 10% palladium on carbon (0.5 g) and 5% platinum on carbon (0.5 g) for 96 hours. The catalysts and solvent were removed and the resulting clear yellow oil was treated with ethereal hydrogen chloride. The hydrochloride was crystallised from methanolethyl acetate to give a pale yellow solid (1.5 g) m.p. 172°–3°.

EXAMPLE 4

5-[1-Hydroxy-2-[(1-methyl-3-phenylpropyl)amino]ethyl]-2-(octyloxy)benzamide, hydrochloride 5-[1-Hydroxy-2-[(1-methyl-3-phenylpropyl)amino]ethyl]-2-(octyloxy)benzamide, hydrochloride was prepared in a manner similar to that described in Example 3(b) from 5-(N, N-dibenzylglycyl)-2-(octyloxy)benzamide. The hydrochloride salt was obtained in a yield of 51%. It had m.p. 173°–174°.

The following ether intermediates were prepared in a similar manner from 5-(N,N-dibenzylglycyl) salicylamide and the alkylating agent indicated in brackets.

5.(a). 5-(N,N-Dibenzylglycyl)-2-[2'-(4-ethoxyphenoxy)ethoxy]benzamide, m.p. 148°–150° [2-(4-ethoxyphenoxy)ethyl bromide].

6.(a) 5-(N,N-Dibenzylglycyl)-2-[2'-(2-ethoxyphenoxy)ethoxy]benzamide, m.p. 130°–132° [2-(2-ethoxyphenoxy)ethyl bromide].

7.(a) 2-[2'-(4-Benzyloxyphenoxy)ethoxy]-5-(N,N-dibenzylglycyl)benzamide, m.p. 122°–130° [2-(4-benzyloxyphenoxy)ethyl bromide].

The following ethers were prepared in a similar manner from the corresponding ether intermediate and benzyl acetone.

5.(b) 2-[2'-(4-Ethoxyphenoxy)ethoxy]-5-[1-hydroxy-2-](1-methyl-3-phenylpropyl)amino]ethyl]benzamide, hydrochloride, sesquihydrate. Foams at 80°.

6.(b) 2-[2'-(2-Ethoxyphenoxy)ethoxy]-5-[1-hydroxy-2-[(1-methyl-3-phenylpropyl)amino]ethyl]benzamide, hydrochloride, decomposes above 60°.

7(b) 5-[1-Hydroxy-2-[1-methyl-3-phenylpropyl)amino]ethoxy]-2-[2'-(4-hydroxyphenoxy)ethyl]-benzamide, hydrochloride, m.p. 170°–174°.

The following Table sets out the activities of a representative number of the compounds described in the preceding Examples using the test described herein.

| Compound | R$_1$ | R$_2$ | R$_3$ | R$_4$ | Equipotent dose relative to propanol β-blockade | |
|---|---|---|---|---|---|---|
| | | | | | β$_1$ heart rate | β$_2$ blood pressure |
| Propianolol | | | | | 1.0 | 1.0 |

-continued

| | $R_4$ | $R_5$ | $R_6$ | $R_7$ | | |
|---|---|---|---|---|---|---|
| Example 3 of UK 1260521 | H | H | —Me | —CH(Me)CH$_2$CH$_2$—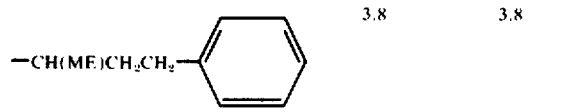 | 3.8 | 3.8 |
| Example 8 of UK 1260521 | H | H | —CH$_2$—CH=CH$_2$ | " | 0.76 | 0.76 |

| | $R_4$ | $R_5$ | $R_6$ | $R_7$ | | |
|---|---|---|---|---|---|---|
| Example 2 | H | H | —CH$_2$CH$_2$O—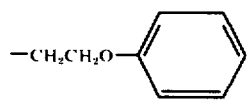 | " | 3 | 100 |
| Example 3 | H | H | —(CH$_2$)$_6$Me | " | 6 | 100 |
| Example 4 | H | H | —(CH$_2$)$_7$Me | " | 5 | 100 |

EXAMPLE 8 Pharmaceutical Composition

Capsules

To prepare 10,000 capsules each containing 25 mg active ingredient.

Mix together 250 g powdered active ingredient with a sufficient quantity of microcrystalline cellulose B.P.C. and fill into No. 3 hard gelatin capsules so that each capsule contains about 120 mg of the mixture.

Capsules may be similarly prepared each containing 50 mg active ingredient.

Tablets

To prepare 5,000 tablets each containing 100 mg active ingredient.

Mix together 500 g active ingredient, 490 g microcrystalline cellulose B.P.C., 5 g magnesium stearate and 5 g stearic acid B.P. Compress the powders on a suitable tabletting press to produce tablets each 6.5 mm in diameter and weighing about 200 mg.

To prepare 5,000 tablets each containing 200 mg active ingredient.

Mix together 1,000 g active ingredient, 500 g lactose and 175 g maize starch, and sufficient of a 2% aqueous solution of sodium hydroxymethyl cellulose to produce a damp cohesive mass. Pass the damp pass through a No. 13 mesh B.S.S. sieve and dry in a fluidised bed dryer at 60° C. Pass the dried granules through a No. 22 B.S.S. sieve and mix with 60 g dried maize starch and 15 g magnesium stearate. Compress the lubricated granules on a suitable tabletting press using 9.5 mm deep concave punches to produce tablets each weighing about 350 mg. These tablets may be film coated with a suitable film forming material such as methyl cellulose, hydroxypropyl, methyl cellulose or mixtures of these materials using standard techniques. The tablets may also be sugar coated by the standard sugar coating techniques.

Injection

To prepare an injection containing 10 mg active ingredient per ml.

Dissolve 10 g active ingredient and 7.5 g sodium chloride in 950 ml water for injections. When solution is complete make up to 1 litre with more water for injections. Subdivide the solution into suitable size ampoules (1 ml, 5 ml or 10 ml) seal and sterilise by heating in an autoclave.

The active ingredient is the compound of Example 2 although this can be replaced by any other compound according to the invention if desired.

We claim:

1. A compound of the formula

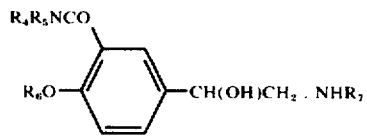

in which:

$R_4$ and $R_5$ independently represent hydrogen or lower alkyl;

$R_6$ represents a group Y(CH$_2$)$_n$, in which n is 2 or 3 and

Y represents a straight or branched chain alkyl group containing 5 carbon atoms optionally substituted with one more hydroxy or alkoxy groups or by aryl groups which may, in turn, contain hydroxy or alkoxy substituents; or Y represents a group ZO—, in which z represents a straight or branched alkyl group containing from 2 to 6 carbon atoms inclusive substituted by one or more alkoxy, hydroxy, or aryloxy groups; or z represents an aryl group which may, optionally, contain one or more hydroxy or alkoxy substituents; and $R_7$ represents a straight or branched alkyl group containing from 3 to 6 carbon atoms, inclusive, optionally substituted by an aryl or aryloxy group which aryl or aryloxy group may, in turn be substituted by hydroxy and alkoxy groups and pharmaceutically acceptable salts thereof.

2. A compound as claimed in claim 1 in which $R_4$ and $R_5$ are hydrogen.

3. A compound as claimed in claim 1 in which $R_6$ represents one of the following groups; $C_7$ or $C_8$ straight chained alkyl, alkoxyalkoxyalkyl, aryloxyalkyl, alkoxyaryloxyalkyl.

4. A compound as claimed in claim 1 in which $R_7$ an aralkyl group.

5. The compound of claim 1 which is 2-[2-(2-ethoxyethoxy)-ethoxy]-5-[1-hydroxy-2-[(1-methyl-3-phenylpropyl)amino]ethyl]benzamide hydrochloride.

6. The compound of claim 1 which is 5-[1-hydroxy-2-[(1-methyl-3-phenylpropyl)amino]ethyl]-2-(2-phenoxyethoxy)-benzamide, hydrochloride.

7. The compound of claims 1 which is 2-(heptyloxy)-5-[1-hydroxy-2-[(1-methyl-3-phenylpropyl)amino]ethyl]-benzamide, hydrochloride.

8. The compound of claim 1 which is 5-[1-hydroxy-2-[(1-methyl-3-phenylpropyl)amino]ethyl]-2-(octyloxy)-benzamide, hydrochloride.

9. The compound of claim 1 which is 2-[2'-(4-ethoxyphenoxy)ethoxy]-5-[1-hydroxy-2-[(1-methyl-3-phenylpropyl)-amino]ethyl]benzamide, hydrochloride, sesquihydrate.

10. The compound of claim 1 which is 2-[2'-(2-ethoxyphenoxy)-ethoxy]-5-[1-hydroxy-2-[(1-methyl-3-phenylpropyl)amino]-ethyl]benzamide, hydrochloride.

11. The compound of claim 1 which is 5-[1-hydroxy-2-[(1-methyl-3-phenylpropyl)amino]ethyl]-2-[2'-(4-hydroxyphenoxy)-ethoxy]benzamide, hydrochloride.

* * * * *